United States Patent
Jiang

(10) Patent No.: US 12,306,085 B2
(45) Date of Patent: May 20, 2025

(54) AUTOMATIC CALIBRATION

(71) Applicant: SOLENTIM LTD., Dorset (GB)

(72) Inventor: Yonggang Jiang, Dorset (GB)

(73) Assignee: SOLENTIM LTD., Dorset (GB)

( * ) Notice: Subject to any disclaimer, the term of this patent is extended or adjusted under 35 U.S.C. 154(b) by 468 days.

(21) Appl. No.: 17/834,822

(22) Filed: Jun. 7, 2022

(65) Prior Publication Data
US 2022/0404258 A1 Dec. 22, 2022

(30) Foreign Application Priority Data
Jun. 8, 2021 (GB) ...................................... 2108156

(51) Int. Cl.
- *G01N 15/10* (2024.01)
- *G01N 15/14* (2024.01)
- *G01N 15/1429* (2024.01)
- *G01N 33/58* (2006.01)

(52) U.S. Cl.
CPC ..... *G01N 15/1012* (2013.01); *G01N 15/1429* (2013.01); *G01N 33/583* (2013.01); *G01N 2015/1006* (2013.01); *G01N 2015/1486* (2013.01)

(58) Field of Classification Search
CPC ........... G01N 15/1012; G01N 15/1429; G01N 33/583; G01N 2015/1006; G01N 2015/1486
See application file for complete search history.

(56) References Cited

U.S. PATENT DOCUMENTS

| | | | |
|---|---|---|---|
| 10,684,207 B2* | 6/2020 | Correia De Matos Nolasco Lamas | G01N 15/1436 |
| 11,995,833 B2* | 5/2024 | Barbash | G06T 5/20 |
| 2010/0189338 A1* | 7/2010 | Lin | G01N 15/1433 382/133 |
| 2013/0194410 A1* | 8/2013 | Topman | G06V 20/69 382/133 |
| 2014/0347463 A1* | 11/2014 | Lin | G06V 20/693 348/79 |
| 2015/0004630 A1* | 1/2015 | Lange | G01N 15/1433 435/40.52 |

(Continued)

FOREIGN PATENT DOCUMENTS

CN 109269964 A 1/2019

OTHER PUBLICATIONS

Search Report dated Mar. 22, 2022, issued in Great Britain Patent Application No. 2108156.7 (3 pages).

*Primary Examiner* — Utpal D Shah
(74) *Attorney, Agent, or Firm* — Lathrop GPM LLP

(57) ABSTRACT

A calibration apparatus comprises estimation circuitry configured to estimate, based on a calibration factor, an estimated number of cells of a first type in a dyed biological sample containing an unknown number of cells. Determination circuitry determines the actual number of cells of the first type in the dyed biological sample. Processing circuitry adjusts the calibration factor. The estimation circuitry is configured with the processing circuitry to estimate the estimated number of the cells of the first type in the dyed biological sample one or more times, based on a different value of the calibration factor for each of the one or more times, until the estimated number of the cells of the first type approaches the actual number of cells of the first type.

12 Claims, 12 Drawing Sheets

(56) References Cited

U.S. PATENT DOCUMENTS

| | | | | |
|---|---|---|---|---|
| 2015/0302237 | A1* | 10/2015 | Ohya | G06T 7/0016 |
| | | | | 382/133 |
| 2017/0261419 | A1* | 9/2017 | Glensbjerg | G01N 15/1436 |
| 2022/0270245 | A1* | 8/2022 | Ishikawa | G06T 7/0012 |
| 2023/0118112 | A1* | 4/2023 | Imai | G01N 15/1433 |
| | | | | 356/343 |
| 2024/0368524 | A1* | 11/2024 | Olszowy | C12M 41/48 |

* cited by examiner

AUTOMATIC CALIBRATION

RELATED APPLICATIONS

This application claims priority to Great Britain Patent Application Number GB 2108156.7, filed Jun. 8, 2021, the entirety of which is hereby incorporated by reference.

TECHNICAL FIELD

The present disclosure relates to a calibration apparatus and a calibration method.

BACKGROUND

The number of cells having particular characteristics in a biological sample needs to be determined for many procedures in biology and medicine, such as cell therapy, determining cell viability and in-process controls in industrial bioprocesses. For example in a cell viability process, the total number of cells in a sample along with the ratio of alive to dead cells may need to be determined.

Many different methods exist in microscopy for the purposes of counting cells having particular characteristics in a biological sample. One such method is the dye exclusion method. This method involves dying biological tissue with a dye that indicates the characteristic in question. For instance, an azo dye (Trypan blue) can be used in order to identify cells that are alive. After staining the sample with Trypan blue, dead cells will remain stained by the dye whereas live cells will become largely uncoloured. This makes it possible to distinguish live cells from dead cells. The number of cells of each type can then be counted. Manual cell counting is still commonplace since it does not require special equipment, but the reproducibility and variability between different users can be high as it relies on the user's ability to distinguish intact cells from cell debris or other particles present in the sample and also determine whether or not a cell is coloured. It is therefore a time consuming process and can lead to variable results. Automated methods of counting the cells have been proposed with the aim of reducing the time required to analyse a sample. A semi-automated dye exclusion method involves using the same dyed biological sample as the manual method described above, but using a digital camera and brightfield imaging to capture a digital image of the sample. The digital image can then be analysed to count the number of live cells in the sample. Whilst this method reduces the time required to analyse a sample it lacks a human's ability to assess, from numerous factors, whether a given entity is a cell, debris, coloured, and so on. Such techniques can therefore be inaccurate.

Accordingly, there is required a simple, efficient, and accurate means of providing a calibrated cell counting method and apparatus.

SUMMARY

Viewed from a first example configuration, there is provided a calibration apparatus comprising: estimation circuitry configured to estimate, based on a calibration factor, an estimated number of cells of a first type in a dyed biological sample containing an unknown number of cells; a determination circuitry configured to determine the actual number of cells of the first type in the dyed biological sample; and processing circuitry configured to adjust the calibration factor, wherein the estimation circuitry is configured with the processing circuitry to estimate the estimated number of the cells of the first type in the dyed biological sample one or more times, based on a different value of the calibration factor for each of the one or more times, until the estimated number of the cells of the first type approaches the actual number of cells of the first type.

Viewed from a second example configuration, there is provided a calibration method comprising: performing an estimation process on a dyed biological sample containing an unknown number of cells to estimate, based on a calibration factor, an estimated number of cells of a first type in the biological sample; performing a determination process on the dyed biological sample to determine an actual number of the cells of the first type in the biological sample; and repeating at least a portion of the estimation process one or more times, based on a different value of the calibration factor for each of the one or more times, until the estimated number of the cells of the first type approaches the actual number of cells of the first type.

Viewed from a third example configuration, there is provided a calibration apparatus comprising: means for performing an estimation process on a dyed biological sample containing an unknown number of cells to estimate, based on a calibration factor, an estimated number of cells of a first type in the biological sample; means for performing a determination process on the dyed biological sample to determine an actual number of the cells of the first type in the biological sample; and means for repeating at least a portion of the estimation process one or more times, based on a different value of the calibration factor for each of the one or more times, until the estimated number of the cells of the first type approaches the actual number of cells of the first type.

BRIEF DESCRIPTION OF DRAWINGS

The present technique will be described further, by way of example only, with reference to embodiments thereof as illustrated in the accompanying drawings, in which.

DETAILED DESCRIPTION

Figure 1A:
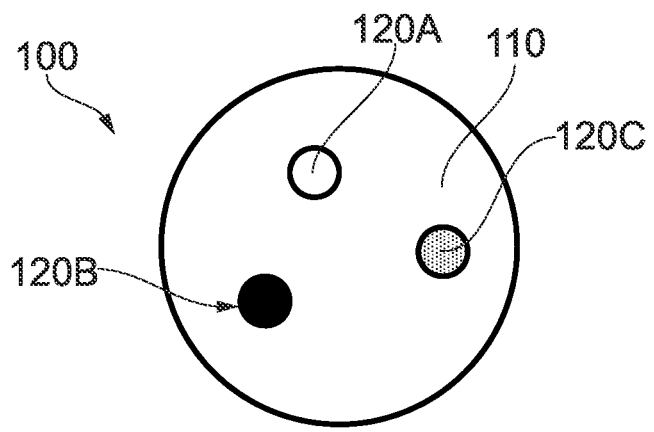
FIGS. 1A-1C illustrate a receptacle containing a biological sample in accordance with some embodiments.

Before discussing the embodiments with reference to the accompanying figures, the following description of embodiments and associated advantages is provided.

According to one aspect there is provided a calibration apparatus comprising estimation circuitry configured to estimate, based on a calibration factor, an estimated number of cells of a first type in a dyed biological sample containing an unknown number of cells. The calibration apparatus also comprises determination circuitry configured to determine the actual number of cells of the first type in the dyed biological sample. The calibration apparatus also comprises processing circuitry configured to adjust the calibration factor. The estimation circuitry is configured with the processing circuitry to estimate the estimated number of the cells of the first type in the dyed biological sample one or more times, based on a different value of the calibration factor for each of the one or more times, until the estimated number of the cells of the first type approaches the actual number of cells of the first type.

In these embodiments, the estimation circuitry uses a calibration factor to perform an estimate of the number of cells of the first type. The accuracy of the estimate is dependent on the calibration factor and once set, the estimation circuitry can be assumed accurate. In order to arrive at the correct calibration factor, the determination circuitry is used to determine the actual number of cells of the first type. By using different calibration factors, the estimation circuitry can perform a number of estimates until the estimates that it produces for the number of cells of the first type approaches the actual value provided by the determination circuitry. The estimation circuitry can then be considered to be calibrated. Future estimates of the number of cells of the first type can then proceed using the estimation circuitry alone. Thus, future estimates of the number of cells of the first type can be produced using a single circuit (for efficiency). Multiple iterations of the calibration process might only use the determination circuitry once. The calibration process may be considered to be complete when the estimated number of cells of the first type is, or (in some embodiments) is within a predefined distance of the actual number of cells of the first type. This predefined distance could be to within an accepted degree of error such as 10%. The dye that is used to dye the biological sample can be, for instance, Trypan blue. However, other possibilities will be known to the skilled person. The dye is typically one that provides an indication to differentiate between the different cell types and may provide differentiation under fluorescent and brightfield imaging.

In some embodiments, the calibration apparatus comprises further determination circuitry configured to determine the total number of cells in the biological sample, and wherein the estimation circuitry is further configured to estimate, based on the calibration factor, an estimated number of cells of a second type in the dyed biological sample containing the unknown number of cells. By determining the total number of cells and estimating or knowing the number of cells of the first type it is possible to know (or estimate) the number of cells of a second, complementary type, by subtraction. In some situations, the number of cells of the first type is calculated for the specific purpose of determining the number of cells of the second type (using the total number of cells as a guide).

In some embodiments the estimation circuitry is further configured with the processing circuitry to determine the estimated number of cells of the first type and the estimated number of cells of the second type in the dyed biological sample one or more times, based on a different value of the calibration factor for each of the one or more times, until the sum of: (i) the estimated number of the cells of the first type and (ii) the estimated number of the cells of the second type approaches the total number of the cells in the biological sample. This provides a further mechanism for determining a correct value of the calibration factor. In particular, since the total number of cells is known then if all cells in the sample are of the first type or the second type, then this provides a further check that the correct calibration factor has been selected. A substance such as Acridine Orange can be used to stain all cells in a sample, and this makes it possible for all of the cells to be made visible under fluorescence imaging. Of course, another technique for making all of the cells visible would be to use a pair of dyes with complementary functions to cause all cells to be made visible. For instance, one could use a first dye that causes live cells to be visible, and a second dye that causes dead cells to be visible. Such an approach has the advantage that, provided the two dyes have different absorption and/or emission spectra, it is possible to make either type of cell visible.

In some embodiments the estimation circuitry comprises an optical microscope and an image capturing device configured to capture a brightfield image of the dyed biological sample. This results in a simple and low cost estimation circuitry. Furthermore, using brightfield imaging (rather than, e.g. fluorescence imaging) can be less complicated, since it does not require the user to perform extra preparations, ensure that dyes are taken up correctly by cells, or ensure that the imaging is performed correctly to capture the fluorescence.

In some embodiments the estimation circuitry is further configured to determine the estimated number of the cells of the first type and the estimated number of the cells of the second type in the biological sample by counting the cells in the brightfield image of the dyed biological sample. As previously explained, brightfield imaging can be easier to perform than other forms of imaging. Hence, once calibration has been performed, estimations as to the number of cells of the first type or the second type can be made with a small amount of complexity.

In some embodiments the estimation circuitry is configured to determine the estimated number of the cells of the second type by counting the colourless cells in the brightfield image of the dyed biological sample and to determine the estimated number of the cells of the first type by counting the contrasted cells in the brightfield image of the dyed biological sample. This allows an estimate of the number of cells of each type to be easily determined, again using brightfield imaging.

In some embodiments the brightfield image of the dyed biological sample is a colour image. This can allow for better distinction between cells and other matter in the biological sample, since more and different types of detail can be illustrated in a colour image.

In some embodiments the brightfield image of the dyed biological sample is a greyscale image. The use of a greyscale image can create a better contrast between cells of the first type and cells of the second type, thereby making the cells of each type easier to distinguish from one another. Furthermore, in some cases, without the need to have imaging capabilities for each colour (red, green, and blue), it may be possible to achieve a higher pixel density, which can in turn lead to sharper images that can make it possible to more easily distinguish cell types.

In some embodiments the determination circuitry comprises a fluorescence microscope and an image capturing device configured to capture a fluorescence image of the dyed biological sample. In some situations, fluorescence imaging can provide a more accurate analysis or count of cells of particular types. For instance, in the case of Trypan blue, fluorescence imaging causes dead cells to fluoresce while live cells (which do not retain the dye) will not fluorescence. Fluorescing cells are easier to identify in images and this technique is less prone to error in terms of identifying the aliveness of cells than brightfield imaging.

In some embodiments the determination circuitry is configured to determine the actual number of the cells of the first type in the biological sample by counting the cells present in the fluorescence image of the dyed biological sample. This allows the number of cells of the first type to be easily determined.

In some embodiments the determination circuitry is configured to determine the actual number of the cells of the first type in the biological sample based on a fluorescent intensity. This allows a threshold to be set for the determination circuitry for what in the fluorescence image corresponds to a cell of the first type. There are a number of ways of expressing fluorescent intensity. For instance, this could be measured as a number of photons within a square area or, in the case of a digital image, a particular intensity of light (e.g. as a greyscale value) that is received for that cell.

In some embodiments the further determination circuitry comprises an optical microscope and an image capturing device configured to capture a fluorescence image of the biological sample. As previously described, a dye such as Acridine Orange (which is visible by fluorescence imaging) can be used to make all cells visible in an image.

In some embodiments the further determination circuitry is configured to determine the total number of the cells by counting the cells in the fluorescence image of the biological sample. This allows the total number of cells in the biological sample to be easily determined.

In some embodiments the estimation circuitry and determination circuitry are configured to operate simultaneously. By performing such analysis in parallel, the overall time required in order to perform calibration can be improved over a system in which the estimation circuitry and determination circuitry operate one after another.

In some embodiments the second type of cells is living cells. As previously described, living cells can be detected by their ability to expel Trypan blue after a period of time has elapsed after exposure. Such cells will therefore appear undyed or will retain only a very small amount of dye around the membrane of the cell (i.e. thereby providing a 'halo' effect with the dye). Other dyes for identifying the liveness of cells also exist and may be used in other embodiments. Furthermore, other embodiments may consider other types for the cell characteristic beyond 'dead'/'alive'. For instance, some embodiments might identify cells based on their purpose or function.

In some embodiments the first type of cells is dead cells. In the case of Trypan blue, a dead cell is not able to expel the Trypan blue from the cell and thus, remain solid or substantially solid. Other dyes for identifying the liveness of cells also exist and may be used in other embodiments. Furthermore, other embodiments may consider other types for the cell characteristic beyond 'dead'/'alive'. For instance, some embodiments might identify cells based on their purpose or function.

The application could also be configured in accordance with the following paragraphs:

In some examples, there is provided a cell analysis apparatus, comprising: image capture circuitry configured to capture a brightfield image of a cell using brightfield imaging, wherein the cell has been dyed by a functional dye that indicates, during fluorescence imaging and during brightfield imaging, whether the cell has a given characteristic; storage circuitry configured to store a model derived by machine learning; and processing circuitry configured to use the model in combination with the brightfield image to determine whether the cell has the given characteristic.

In these examples, the model provides a correspondence between a characteristic (e.g. a biological characteristic) and brightfield images of cells that have been dyed with a functional dye, with the cells having the particular characteristic. Such a model can be derived by machine learning techniques. Fluorescence imaging can be more accurate than brightfield imaging. However, fluorescence imaging is more difficult and complicated to perform. The present techniques therefore relate to the generation of a model (via the use of machine learning techniques) in which there is a correspondence between a given characteristic and a brightfield image. This makes it possible to more accurately detect the given characteristic from brightfield images without the need to perform more complicated fluorescence imaging. There is no need for the apparatus that uses the model to be the device that trains the model—although clearly a similarity in equipment (e.g. imaging devices) is likely to lead to more accurate application of the developed model and therefore more accurate predictions using the model. The form of storage need not be non-volatile storage and could include volatile storage. A functional dye can be considered to be a dye that is used to reveal a particular characteristic of a cell. For instance, a functional dye might be used to reveal whether a cell is of a particular type, whether it has a particular configuration, or whether it exhibits a particular attribute (e.g. being alive or dead, for instance). In some cases such a dye may become visible when the characteristic is present and in other cases the dye may become visible when the characteristic is not present. In some cases, the functional dye might begin visible (or invisible) and the visibility might reverse given a period of time, depending on the presence of the characteristic. Some functional dyes might be non-binary. For instance, a dye might change to multiple colours depending on the presence of different characteristics. The intensity or particular shade of a dye might be used to indicate particular characteristics—in a similar way to how a pH indicator might use different shades to indicate different pHs. In any case, the application of the dye is not always entirely unambiguous, although may generally be considered to be sufficiently accurate for the purposes of biological studies. In these examples, the functional dyes provide indications under both fluorescence imaging and brightfield imaging, although the indication need not be the same in both types of images.

In some examples, the brightfield image is a colour image. As previously explained, some functional dyes might turn different shades depending on the characteristic being detected in a similar way to how a pH indicator might turn red in the presence of an acid, and violet in the case of an alkali. In these situations, a colour image might be necessary in order to apply the image to the model in order to determine whether the characteristic is present.

In some examples, the brightfield image is a greyscale image. Where colour is not essential—for instance where the dye either remains or does not remain in a cell, the use of colour might not be of particular use. In these situations, it might be more useful to instead have a high contrast image. This can be achieved by using a greyscale brightfield image rather than a colour image.

In some examples, the given characteristic of the cell is that the cell is dead. This might, for instance, be determined either by actively detecting for cell death or by actively detecting for cell liveness.

In some examples, the functional dye is an azo dye. For instance, in some examples, the functional dye is Trypan blue. It is observed that Trypan blue can be used for the classification of liveness in both fluorescence imaging and brightfield imaging (albeit it is clearer to distinguish in fluorescence imaging). The Trypan blue dye is expelled from live cells after a period of time. In contrast, dead cells are unable to expel the dye. Consequently, after having applied the dye to cells, it is possible to determine whether the cells are alive or dead by whether the cells remain dyed or not. In the case of brightfield imaging, this can be more difficult to determine since the dye can continue to cling to the surface of live cells thereby creating a 'halo' effect. In contrast, in fluorescence imaging, live cells can be distinguished from dead cells more easily. Similarly, this can be difficult to determine since cells transition from alive to dead over time and so the status of some cells can be ambiguous and difficult for a human to assess consistently.

In some examples, the model has been trained using fluorescence images and brightfield images. As previously explained, fluorescence images can be used to more accurately determine whether a given characteristic is present in a cell or not. Consequently, by performing training using pairs of fluorescence/brightfield images, the brightfield images can be used to perform the training, while the fluorescence imaging is used to determine whether the given characteristic is present or not. In this way, a large portion of training data can be automatically generated in order to train a model to detect the given characteristic from brightfield images that would be expected to be approximately as accurate as analysis done using fluorescence imaging, without the associated complexities of fluorescence imaging being necessary.

In some examples, the model comprises a set of weights or parameters derived by using a neural network. For instance, the neural network could be a convolutional neural network. These types of machine learning models can be particularly well suited to image analysis.

In some examples, there is provided a method for creating a cell categorisation model, comprising applying a functional dye to one or more samples comprising a plurality of cells, wherein the functional dye is configured to indicate, during fluorescence imaging and during brightfield imaging, whether each of the cells has a given characteristic; capturing a brightfield image and a corresponding fluorescence image for each of the plurality of cells to which the dye has been applied; and using a machine learning process to generate a model that predicts whether a cell has the given characteristic from a brightfield image, wherein the model is generated by using the brightfield image and the corresponding fluorescence image of each of the plurality of cells as training data.

The above method can therefore be used to generate the model that provides a correspondence between the characteristic and the brightfield images taken of cells to which the functional dye has been applied. The fluorescence images are used to determine whether the characteristic is present or not, obviating the need for human intervention to specify whether the characteristic is present or not in the corresponding brightfield image and thereby enabling a large amount of training data to be quickly generated with which a model can be trained. The generated model can then be used in an apparatus (either the same apparatus that generated the model or another apparatus altogether) in order to determine whether the characteristic exists using brightfield images with the dye applied. Since the application of the model (after it has been devised) does not require fluorescence imaging to take place, the complexities associated with fluorescence imaging need not take place. Meanwhile the operator of the model can determine whether the characteristic is present or not with a higher accuracy and repeatability than can normally be determined with brightfield imaging.

In some examples, the model comprises a set of weights or parameters derived by using a neural network. For instance, the neural network could be a convolutional neural network. These types of machine learning models can be particularly well suited to image analysis.

Particular embodiments will now be described with reference to the figures.

Note that throughout this description, the term "cell" is used. However, the present technique relates equally to particles other than cells, which could be provided in a growth medium or other suspension.

Figure 1B:
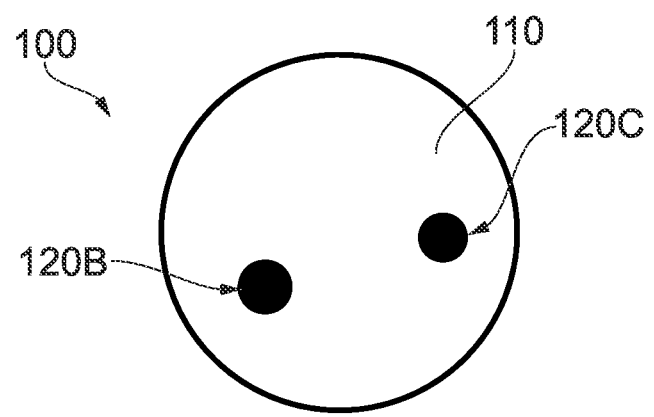
Figure 1C:
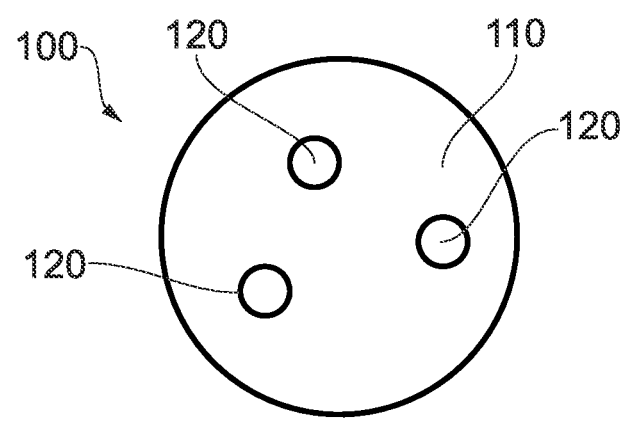

FIGS. 1A, 1B, and 1C illustrate a receptacle 100 containing a biological sample 110 in accordance with some embodiments. There are two types of cell within the biological sample 110, a second type 120A and a first type 120B (the two types being mutually exclusive in this case), and the total number of cells within the biological sample 110 along with the number of cells of the second type 120A and the number of cells of the first type 120B is initially unknown. In some examples, the second type 120A of cells is living cells and the first type 120B of cells is dead cells. In this example, a dye (e.g. an azo dye such as Trypan blue) is applied to the biological sample 110 in order to distinguish between the cells of the second type 120A and the cells of the first type 120B. In this example, both types 120A, 120B of cell absorb the dye. However, live cells 120A expel the dye while the dead cells 120B do not. Consequently, the dead cells 120B appear contrasted to the cells of the second type 120A when viewed under an optical microscope or using regular (e.g. brightfield) imaging.

An estimation process can be performed, which involves capturing a brightfield image of the dyed biological sample 110, for example using an optical microscope and an image capturing device, such as a digital camera, to capture an image of the biological sample 110 illuminated by white light. The brightfield image may be a colour image, where the second type 120A of cells appear colourless (e.g. white) and the first type 120B of cells appear contrasted, (e.g. coloured by the colour of the dye). Alternatively, the brightfield image may be a greyscale image, where the second type 120A of cells appear colourless (e.g. white or light grey) and the first type 120B of cells appear contrasted (e.g. dark grey or black). The estimated number of cells of the second type 120A (e.g. living cells) can be estimated by counting the number of cells that are uncoloured in the brightfield image and the estimated number of cells of the first type 120B (e.g. dead cells) can be estimated by counting the number of cells that are coloured or contrasted in the brightfield image. This can be done by any conventional image analysis and processing methodology such as by edge detection or by looking for groups of contrasted or differently coloured pixels as compared to their surroundings. However, the question as to whether a cell is coloured or not is dependent on the calibration factor and specifically, what counts as 'coloured' or 'contrasted'.

FIG. 1A illustrates an image of the receptacle 100 containing a biological sample 110 as captured during the estimation process. A number of cells 120 are present in the biological sample 110, and they appear either light or contrasted depending on whether they are cells of the second type 120A or the first type 120B, and therefore whether they have expelled the dye applied to the biological sample. In order to determine whether the boundary between whether a given cell is determined to be a cell of the second type 120A or a cell of the first type 120B, a calibration factor is set to determine the shading or level of brightness at which a cell is determined to be a cell of a particular type. In the example illustrated in FIG. 1A, cell 120C may be determined to be a cell of the second type 120A or a cell of the first type 120B depending on the calibration factor. The calibration factor can be associated with the image analysis and processing methodology used with the brightfield image, for example related to the pixel intensity value or colour contrast of the brightfield image. For example, the calibration factor could be proportional to the number and/or wavelength of photons emitted from the portion of the sample that the image pixel corresponds to.

In these examples, a determination process involves capturing a fluorescence image of the dyed biological sample 110, for example using an optical microscope and an image camera device, such as a digital camera, to capture an image of the biological sample 110 illuminated by fluorescence. The image capture device could be the same image capture device as used in the estimation processor or it may be a different image capture device. Having performed the fluorescence imaging, the number of cells of the first type 120B can be determined as a matter of fact by counting the cells present in the fluorescence image of the dyed biological sample 110. The present technique recognises that Trypan blue is fluorescent and provides a cell characteristic indication under both fluorescent imaging and brightfield imaging. Consequently, the cells of the first type 120B, which retain the dye, are clearly visible on the fluorescence image whilst the cells of the second type 120A, which do not absorb (or which expel) the dye, do not appear (or appear very faintly) on the fluorescence image. Accordingly, the cells clearly visible on the fluorescence image are the cells of the first type 120B, and therefore by counting all of the cells clearly present in the fluorescence image, the number of cells of the first type 120B in the biological sample 110 can be accurately determined without the use of the previously described calibration factor. The determination of the number of cells of the first type present in the fluorescence image of the dyed biological sample 110 may be based on a fluorescent intensity. For example, a measure such as photons per area per second is linearly related to the fluorescent intensity. This objective measure sets a cut off between the range of fluorescent intensities which corresponds to a cell of the first type and should therefore be included in the count of cells of the first type, and the range of fluorescent intensities which do not correspond to a cell of the second type and should thus be ignored in the count of cells of the second type. However, it will be appreciated that this objective measure typically does not vary under controlled conditions, such as when the quantity of cell dye introduced is at a specific concentration, the light use to illuminate the sample is at a calibrated intensity etc. In particular, the use of fluorescence imaging to determine cell liveness' provides a more objective measure of whether a cell is alive or not than brightfield imaging.

FIG. 1B illustrates an image of the receptacle 100 containing a biological sample 110 as captured by the determination process. A number of cells 120 are present in the biological sample 110, but as the determination process uses fluorescence to capture the image, only those cells that have retained the dye applied to the biological sample 110 will appear clearly in the image, since it is the dye which gives the cells the fluorescent properties. Accordingly, only the cells of the first type 120B present in the biological sample 110 can be determined from the determination process. As illustrated in FIG. 1B, cell 120C has been captured in the image generated by the determination process, and therefore it can be determined that cell 120C is a cell of the first type 120B.

The number of cells of the first type 120B in the biological sample 110 determined by the determination process can then be compared to the estimated number of cells of the first type 120B in the dyed biological sample 110 determined by the estimation process. Since the fluorescence and brightfield images also correspond (e.g. cover the same view of the sample), it is also possible to perform as a pixel-by-pixel comparison between the two images to see which pixels in the fluorescence image that are identified as part of a 'dead cell' are similarly identified in the brightfield image.

The information provided by the determination process can therefore be used to change the calibration factor (possibly repeatedly) used in the estimation process, until the estimation process and the determination process both produce results for the number of cells of the first type 120B that approach one another. The term "approaches" is understood to mean that the estimated number of the cells of the first type 120B matches the actual number of cells of the first type 120B to within an appropriate margin of error, for example ±5 cells, ±10 cells, ±100 cells, ±1000 cells.

For example, consider a situation in which the calibration factor represents an intensity of a set of pixels required to consider a cell as 'dead'. If the estimate falls far below the determination then the calibration could be adjusted by −10 (making it easier to identify a set of pixels as a dead cell) and a portion of the estimation process could then be repeated using the revised calibration factor. If the estimate still falls sufficiently far below the determination then the calibration amount might be adjusted by the same amount again. Alternatively, if the new estimated number of the cells of the first type 120B is now greater than the actual number of cells of the first type 120B and outside the appropriate margin of error, the calibration factor may be adjusted to a negative fraction of the amount of the previous adjustment, such as a half (e.g. +5). In general, any form of iterative method of adjusting the calibration factor can be employed such that the estimated number of the cells of the first type 120B approaches the actual number of cells of the first type 120B.

The same brightfield image could be used each time and the calibration factor adjusted each time until the estimated number of the cells of the first type 120B approaches the actual number of cells of the first type 120B. In such an example, the image capturing process for the determination process need only be performed once. Alternatively, the calibration factor may be associated with the optical microscope or the image capturing device used to generate the brightfield image. In this case, an image will be captured each time the process is repeated, based on a different value of the calibration factor each time the estimation process is repeated, and the image analysis and processing methodology performed in the same way each time the process is repeated. Accordingly, different portions of the estimation process may be repeated depending on component the calibration factor is associated with.

In the example illustrated in FIG. 1B, there are two cells of the first type 120B present in the biological sample as it can be determined that cell 120C is a cell of the first type 120B. If cell 120C is considered, by the estimation process, to be a cell of the second type 120A then the estimation process would only estimate that there is one cell of the first type present in the biological sample. Since this would differ from the actual number of cells of the first type 120B determined by the determination process, the calibration factor associated with the estimation process would be adjusted. The estimation process is then repeated and the results compared to the determination process without having to repeat the determination process. The estimation process can be repeated as many times as required until the estimated number of cells of the first type 120B matches the actual number of cells of the first type 120B determined by the determination process. This acts as an indicator that the estimation process is calibrated and the estimation process can then be performed on different biological samples without having to perform the determination process on each different biological sample. This is advantageous since the estimation process can determine the number of cells of the second type 120A. This is further advantageous when the estimation process uses brightfield imaging and the determination process uses fluorescence imaging, because brightfield imaging is easier to perform.

Since the estimation process and the determination process are performed on the dyed biological sample 110, the estimation process and the determination process can be performed simultaneously. In the context of the present application, simultaneously is understood to mean that a portion of the estimation process by be performed at the same time as a portion of the determination process. For example, the determination process may be begun whilst the estimation process is being performed, thereby overlapping the running of the processes. Alternatively, the estimation process and the determination process could commence at substantially the same time or a portion of the estimation process and the determination process could be performed before the next portion of the estimation process and the determination process is performed. For example, the brightfield image could be captured as part of the estimation process and the fluorescence image captured as part of the determination process before the number of cells are determined in each process. In some examples where the same image capture device is used to capture the brightfield image as part of the estimation process and the fluorescence image as part of the determination process, both images could be captured by the same image capture device before the images are analysed in order to determine the number of cells in each image In some examples, the calibration method further comprises performing a further determination process on the biological sample 110 to determine the total number of cells in the biological sample 110. This makes it possible to perform additional calibration tests. FIG. 1C illustrates an image of the receptacle 100 containing a biological sample 110 as captured by the further determination process. A number of cells 120 are present in the biological sample 110, but only the total number of cells 120 present in the biological sample 110 can be determined from the further determination process. That is, the further determination process does not directly determine the types of the cells but by knowing the total number of cells and the number of cells of the first type 120B, it is possible to infer the actual number of cells of the second type 120A. At least a portion of the estimation process is repeated one or more times, based on a different value of the calibration factor for each of the one or more times, until the sum of the estimated number of the cells of the first type and the estimated number of the cells of the second type approaches the total number of the cells in the biological sample. The adjustment of the calibration factor and the portions of the estimation process to be repeated are the same as described above.

There are a number of techniques that can be used for revealing all cells in a biological sample. For instance, a general-purpose dye such as Acridine Orange can be use in fluorescence imaging to cause all cells to fluoresce. As an alternatively, a combination of dyes could be used, again in fluorescence imaging—with one dye being used (for instance) to cause live cells to fluoresce and another dye being used to cause dead cells to fluoresce.

The further determination process, in this example, includes capturing a fluorescence image of the biological sample 110, for example using an image capture device such as a digital camera (possibly in combination with an optical microscope) to capture an image of the biological sample 110. The optical microscope may be the same optical microscope as used in the estimation processor it may be a different optical microscope. The image capture device may be the same image capture device as used in the estimation process and/or the determination process or it may be a different image capture device. The total number of cells in the biological sample 110 can be determined by counting the number of cells in the image of the biological sample 110.

The total number of cells in the biological sample 110 determined by the further determination process can then be compared to the sum of the estimated number of the cells of the second type 120A and the estimated number of cells of the first type 120B determined by the estimation process. When the total number of cells determined by the further determination process and the estimation process are different, the calibration factor associated with the estimation process can be adjusted in order to improve the accuracy of the estimations in the estimation process. In particular, the total number of cells determined by the further determination process and the estimation process should be the same if the same biological sample 110 is used. A difference could be caused, for example, by cell debris or other particles present in the biological sample 110 being included in the estimates in the estimation process, or by the use of the dye itself causing interference in the imaging of the estimation process. If a difference exists, the estimation process can be repeated with the adjusted calibration factor and the new estimated total number of cells compared to the total number of cells determined by the further determination process without having to repeat the further determination process. The estimation process can be repeated as many times as required (each time with different calibration factors) until the estimated total number of cells matches the total number of cells. This acts as another indicator that the estimation process is calibrated and the estimation process can then be performed on different biological samples without having to perform the further determination process on each different biological sample. This is advantageous since the estimation process can determine the number of cells of both the second type 120A and the first type 120B.

Since the further determination process determines the total number of cells in the biological sample 110 and the determination process determines the total number of cells of the first type 120B in the biological sample 110, the total number of cells of the second type 120A can be determined by subtracting the number of cells of the first type 120B determined in the determination process from the total number of cells determined in the further determination process. The total number of cells of the second type 120A can then be compared with the estimated number of cells of the second type 120A from the estimation process. If there is a difference then the calibration factor associated with the estimation process can again be adjusted. The estimation process can then be repeated and the new estimated number of cells of the second type 120A compared to the total number of cells of the second type 120A without having to repeat the further determination process. The estimation process can be repeated as many times as required, each time adjusting the calibration factor, until the estimated number of cells of the second type 120A matches the total number of cells of the second type 120A. This acts as a further indication that the estimation process is calibrated and the estimation process can then be performed on different biological samples without having to perform the determination process or the further determination process on each different biological sample. This is advantageous since the estimation process can determine the number of cells of both the second type 120A and the first type 120B in a single process.

Figure 2:
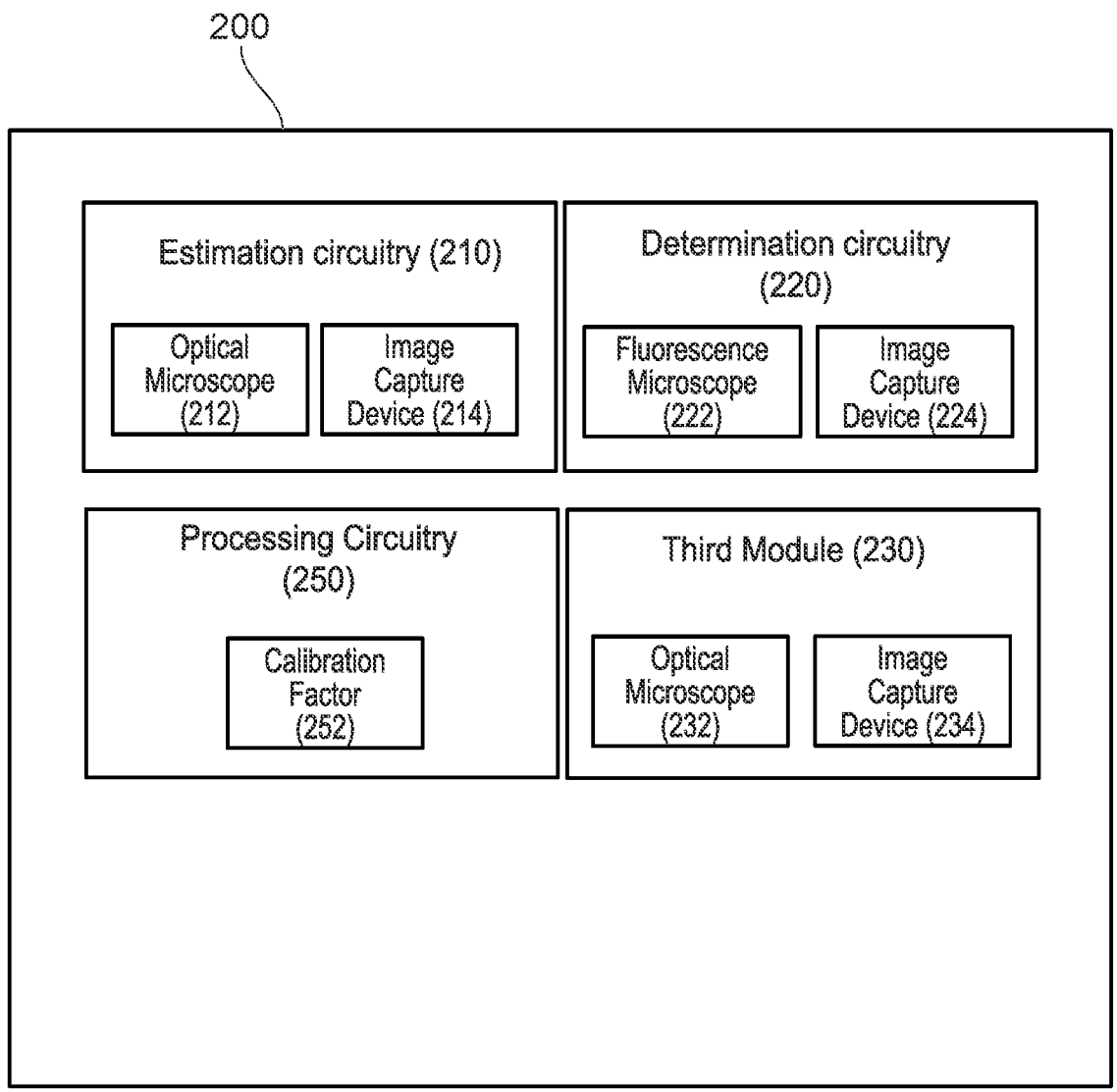
FIG. 2 illustrates an example apparatus in accordance with some embodiments.

FIG. 2 illustrates an example apparatus 200 in accordance with some embodiments. The calibration apparatus 200 comprises an estimation circuitry 210 configured to determine an estimated number of cells of a second type 120A in a dyed biological sample 110 containing an unknown number of cells. The calibration apparatus 200 also comprises a determination circuitry 220 configured to determine the actual number of cells of the first type 120B in the dyed biological sample 110. The calibration apparatus 200 further comprises processing circuitry 250 configured to adjust a calibration factor 252 associated with the estimation circuitry 210 when the estimated number of cells of the first type 120B is different to the actual number of cells of the first type 120B in the dyed biological sample 110.

The estimation circuitry 210 may comprise an optical microscope 212 and/or an image capturing device 214 for capturing a brightfield image of the dyed biological sample 110. The estimation circuitry 210 can then be used to determine the estimated number of cells of the second type 120A and the estimated number of cells of the first type 120B in the biological sample 110 by counting cells in the brightfield image of the dyed biological sample 110, for example by counting colourless cells in the brightfield image of the dyed biological sample 110 and by counting contrasted cells in the brightfield image of the dyed biological sample 110 respectively.

Equally, the determination circuitry 220 may comprise a fluorescence microscope 222 and an image capturing device 224 for capturing a fluorescence image of the dyed biological sample 110. The determination circuitry 220 can then be used to determine the actual number of cells of the first type 120B in the biological sample 110 by counting cells present in the fluorescence image of the dyed biological sample 110.

In some examples, the calibration apparatus 200 also comprises further determination circuitry 230 configured to determine the total number of cells in the biological sample 110. The processing circuitry 250 is then further configured to adjust the calibration factor 252 associated with the estimation circuitry 210 when the sum of the estimated number of cells of the second type 120A and the estimated number of cells of the first type 120B is different to the total number of cells in the biological sample 110.

The further determination circuitry 230 may comprise an optical microscope 232 and an image capturing device 234 for capturing a brightfield image of the biological sample 110. The further determination circuitry 230 can then be used to determine the total number of cells by counting cells in the biological sample 110.

The estimation circuitry 210 and the determination circuitry 220 could be combined into the same device within the calibration apparatus 200 or could share components with each other or with other elements of the apparatus 200 in any combination. For example, as described above, the estimation circuitry 210 and the determination circuitry 220 could use the same image capture device. This is advantageous since the cells in the biological sample 110 could be in suspension, and therefore it is desirable to minimise movement of the biological sample 110 in order to avoid influencing the accuracy of the imaging. The further determination circuitry 230 could also be incorporated into the same device as the estimation circuitry 210 and determination circuitry 220, further reducing the amount of movement of the biological sample 110 required. For example, the estimation circuitry 210 and the further determination circuitry 230 may use the same optical microscope whilst the further determination circuitry 230 may use the same image capture device as at least one of the estimation circuitry 210 and the determination circuitry 220. An automated means of applying the dye to the biological sample 110, such as an automated pipetting system, can be incorporated into the device in order to further reduce the amount of movement of the biological sample 110 required.

Although the calibration factor 252 is illustrated in FIG. 2 as forming part of the processing circuitry 250, in some embodiments it may be separate from the processing circuitry, for example contained within the estimation circuitry 210 or the component within the estimation circuitry 210 the calibration factor 252 relates to, such as the optical microscope 212 and the image capturing device 214.

Figure 3:
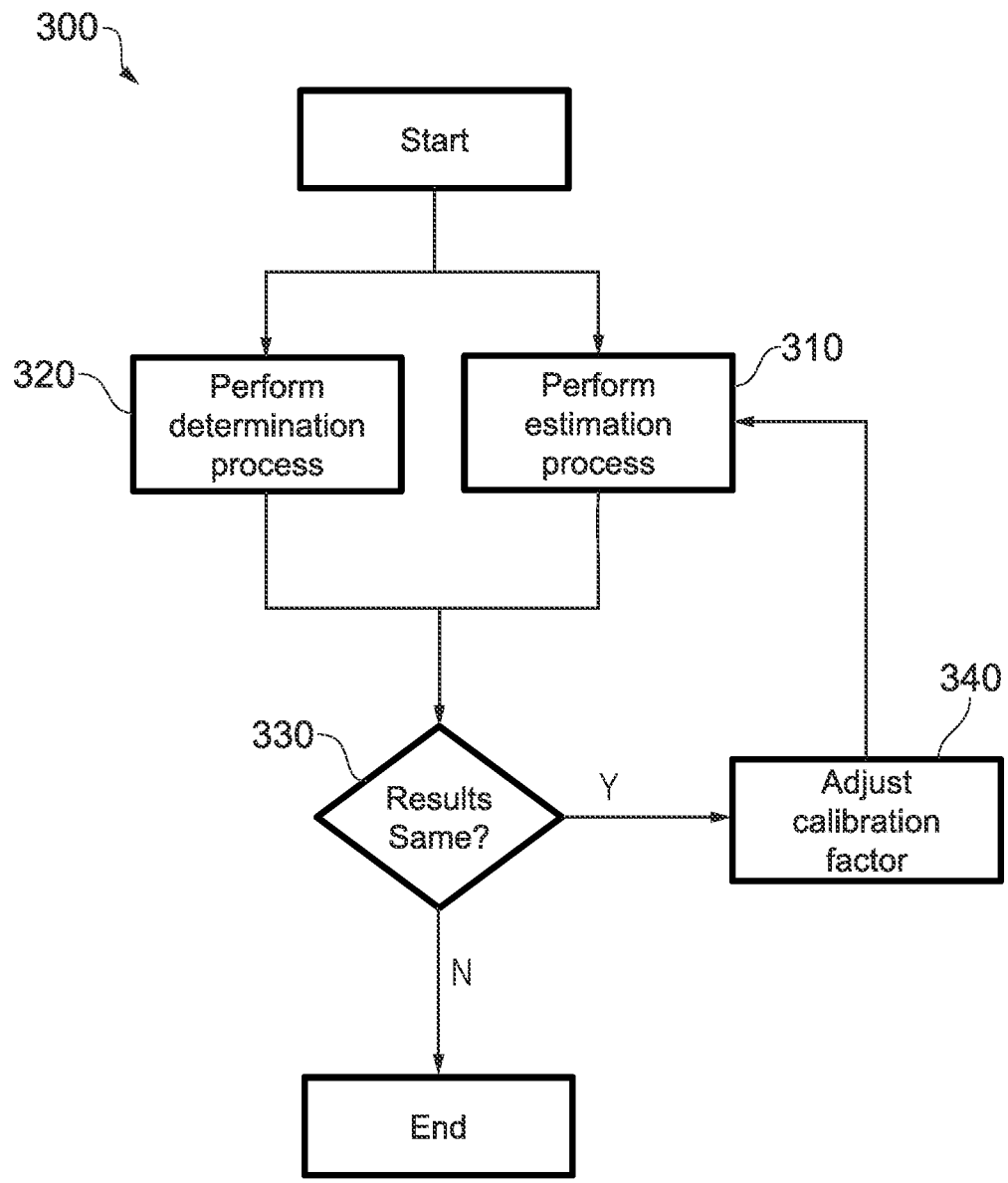
FIG. 3 is a flow chart of a calibration method in accordance with some embodiments.

FIG. 3 is a flow chart of the calibration method 300 according to the first aspect. The method begins at step 310 where an estimation process is performed on a dyed biological sample containing an unknown number of cells to determine an estimated number of cells of a first type. At step 320 a determination process is performed on the dyed biological sample to determine the actual number of cells of the first type in the biological sample. Although step 320 is illustrated as being at the same time as step 310, these steps may be performed simultaneously as described above or separately. At step 330 the estimated number of cells of the first type determined by the estimation process is compared to the actual number of cells of the first type in the biological sample determined by the determination process. If the results of the estimation process and the determination process are the same, or within an appropriate margin of error as described above, the method ends. If the results of the estimation process and the determination process are different or outside the appropriate margin of error, the method continues to step 340 where the calibration factor associated with the estimation process is adjusted and the method returns to step 310, where at least a portion of the estimation process is repeated with the different, adjusted calibration factor. Steps 330, 340 and 310 of the method are then repeated as many times as required until the results of the estimation process and the determination process are the same, or within an appropriate margin of error. Although not shown in the flow chart of FIG. 3, it will be appreciates that the total number of iterations could be limited so as to inhibit an infinite loop from occurring in a case where there is no calibration factor that achieves acceptable results.

Figure 4:
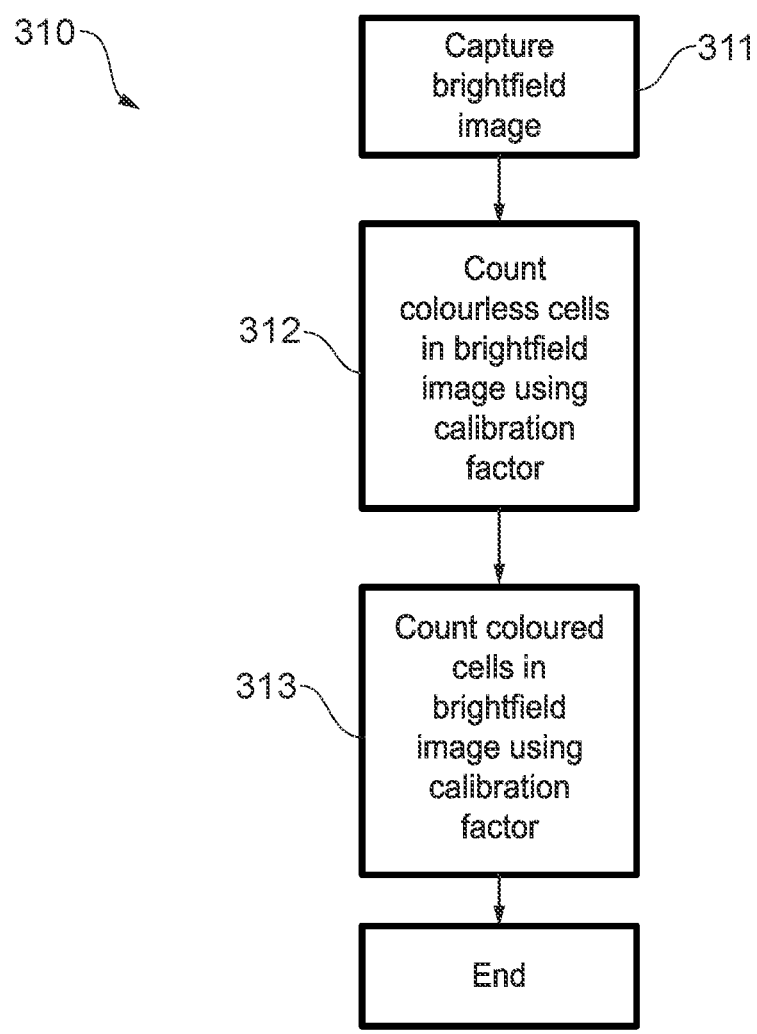
FIG. 4 is a flow chart showing step 310 of the calibration method shown in FIG. 3 in more detail.

FIG. 4 is a flow chart showing a variant of step 310 of the calibration method 300 shown in FIG. 3. At step 311 a brightfield image of the dyed biological sample is captured, for example using an optical microscope 212 and an image capturing device 214. At step 312 the estimated number of cells of the second type in the biological sample is determined by counting the colourless cells in the brightfield image of the dyed biological sample captured in step 311 using a current calibration factor in order to decide whether each cell is coloured/contrasted or not. At step 313 the estimated number of cells of the first type in the biological sample is determined by counting the coloured cells in the brightfield image of the dyed biological sample captured in step 311. This again makes use of the calibration factor to decide whether a cell is coloured/contrasted or not.

Figure 5:
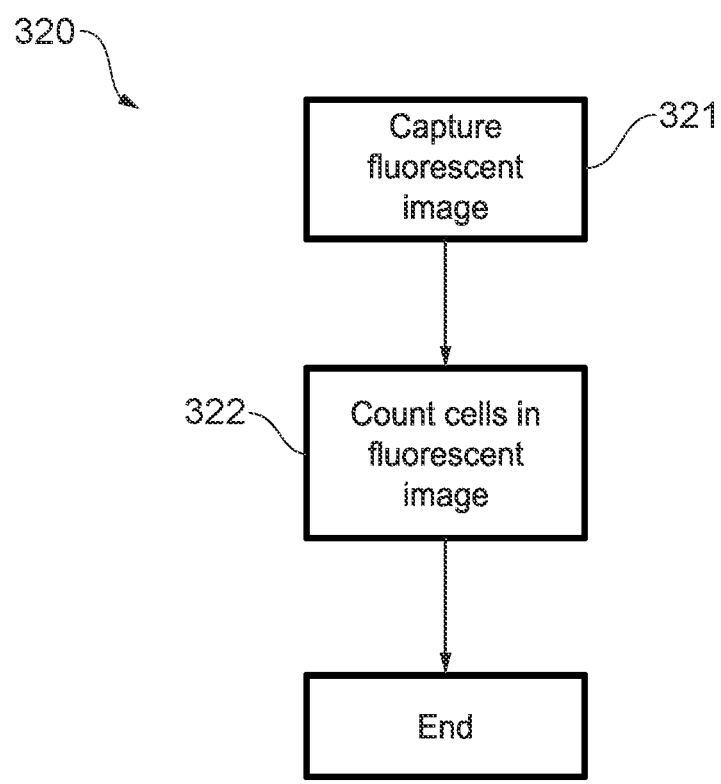
FIG. 5 is a flow chart showing step 320 of the calibration method shown in FIG. 3 in more detail.

FIG. 5 is a flow chart showing step 320 of the calibration method 300 shown in FIG. 3 in more detail. At step 321 a fluorescence image of the dyed biological sample is captured, for example using a fluorescence microscope 222 and an image capturing device 224. At step 322 the number of cells of the first type in the biological sample is determined by counting the cells in the fluorescence image of the dyed biological sample captured in step 321.

Figure 6:
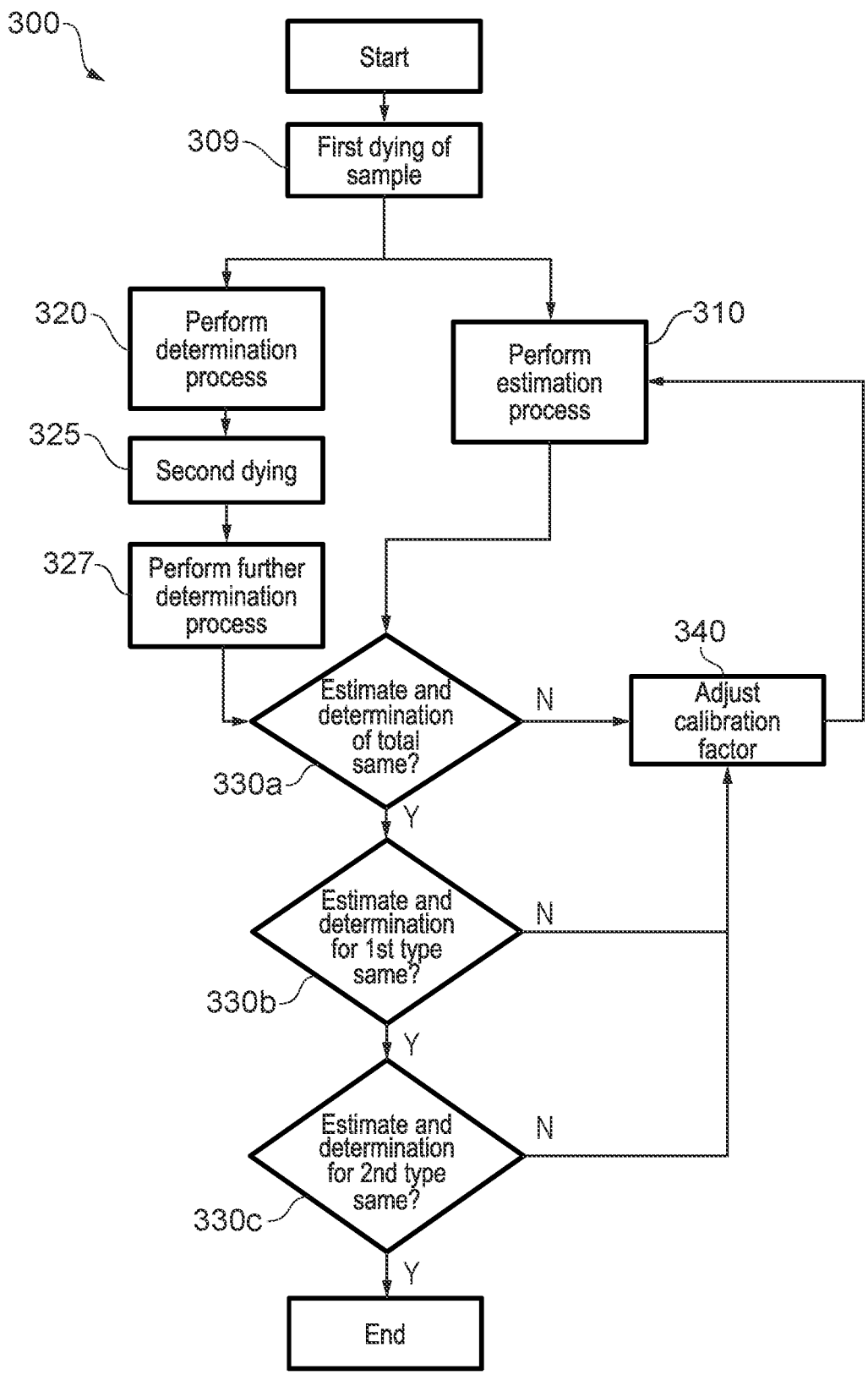
FIG. 6 is a flow chart of the calibration method shown in FIG. 3 in further detail.

FIG. 6 is a flow chart that shows alternative embodiments of the calibration method 300 shown in FIG. 3. The method begins at step 309 where the biological sample is dyed for the cells of the first type to be determined. The method then continues to step 310 where an estimation process is performed on the dyed biological sample to determine an estimated number of cells of the first type and an estimated number of a second type in the biological sample. Simultaneously, at step 320, a determination process is performed on the dyed biological sample to determine the actual number of cells of the first type in the biological sample. A second dying then takes place at step 325 to cause all cells to be revealed, and at step 327, a further determination process is performed to determine the actual total number of cells.

Although steps 310 and steps 320, 325, and 327 are illustrated as being performed simultaneously, they may be performed sequentially, for example step 310 prior to step 320, or a portion of step 310 may be performed before a portion of step 320. However, it is generally desirable for the estimation process 310 to be complete before the second dying takes place at step 325 so as to not corrupt the estimation process 310. At step 330a, the results of the estimation process are compared to the results of the further determination process by comparing the sum of the estimated number of cells of the first type and the estimated number of cells of the second type determined from the estimation process with the total number of cells determined from the further determination process. If the results are different, or outside the appropriate margin of error, the method continues to step 340, where a calibration factor associated with the estimation process is adjusted, before the method continues back to step 310 where at least a portion of the estimation process is performed again with the different, adjusted calibration factor. If, at step 330a, the results of the estimation process and the further determination process are the same, or within an appropriate margin of error, the method continues to step 330b. At step 330b the results the estimation process are compared to the results of the determination process by comparing the estimated number of cells of the first type from the estimation process with the actual number of cells of the first type from the determination process. If the results are different, or outside the appropriate margin of error, the method continues to step 340, where a calibration factor associated with the estimation process is adjusted, before the method continues back to step 310 where at least a portion of the estimation process is performed again. If, at step 330b, the results of the estimation process and the determination process are the same, or within an appropriate margin of error, the method continues to step 330c. At step 330c the results of the estimation process are compared to the results of the determination process by comparing the estimated number of cells of the second type from the estimation process with the actual number of cells of the second type (i.e. by subtracting the result of the further determination process that determines the total number of cells from the result of the determination process that determines the number of cells of the first type). If the results are different, or outside the appropriate margin of error, the method continues to step 340, where a calibration factor associated with the estimation process is adjusted, before the method continues back to step 310 where at least a portion of the estimation process is performed again. If, at step 330c, the results are the same or within an appropriate margin of error, the method ends and the estimation process is considered to be calibrated. The appropriate margin of error at each of steps 330a, 330b, 330c could be unique or could be shared among either or both of the other steps. Having completed the calibration process, the estimation process can then be used to process other biological samples without having to perform the determination process or the further determination process again and without having to adjust a calibration factor associated with the estimation process again. The ordering of steps 330a, 330b, and 330c could also be varied.

Figure 7:
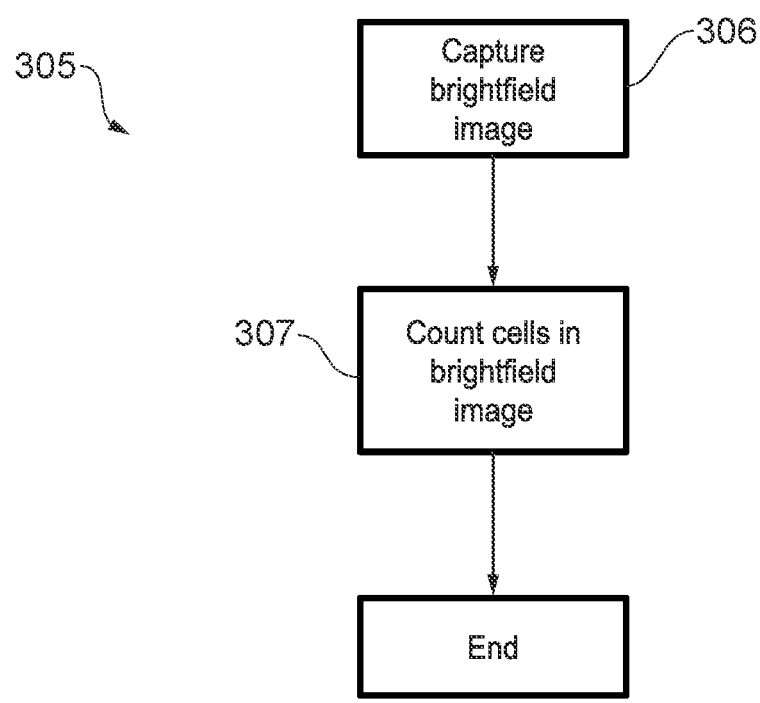
FIG. 7 is a flow chart showing step 305 of the calibration method shown in FIG. 6 in more detail.

FIG. 7 is a flow chart showing step 320 of the calibration method 300 shown in FIG. 6 in more detail. At step 306 an image of the biological sample is captured, for example using an optical microscope 232 and an image capturing device 234. At step 307 the total number of cells in the biological sample is determined by counting the cells in the image of the biological sample captured in step 306.

The calibration method as described above may be implemented by one or more computers. A computer program may be provided for controlling a computer to perform the calibration method. A computer readable storage medium may also be provided for storing the computer program. The computer readable storage medium may be non-transitory. A computer program product may also be provided for controlling a computer to perform the calibration method.

According to the above description, it is possible to use a calibration factor to adjust a "sensitivity" of a parameter used with a brightfield image to determine whether a cell count in the brightfield image matches a cell count in a fluorescence image. When the calibration factor causes the two counts to match, it can be said that brightfield imaging produces an accurate estimate without the need for fluorescence imaging. Further imaging can then take place using brightfield imaging. Although the example of Trypan blue has been provided, which the inventors of the present technique have discovered can lead to accurate results in brightfield imaging, these techniques can also be used with, for instance, other functional dyes. For instance, a functional (fluorescent) dye could be used to characterise the mitotic index of cells, which can then be determined in brightfield imaging according to the size of those cells. The calibration factor could be, for instance, a radius of a cell. The fluorescence imaging would produce a 'truth' as to the actual mitotic index and the calibration factor could be modified until the mitotic index estimated using brightfield imaging corresponds (within the accepted level of error) to the mitotic index determined by the fluorescence imaging.

The calibration factor could be determined according to a series of weights or parameters determined using machine learning. In such examples, an apparatus is used to quickly generate images of biological samples that have been stained with a functional dye such as Trypan blue using both fluorescence imaging and brightfield imaging to generate fluorescence/brightfield image pairs. These pairs of images can be used in order to produce a training set. In particular, within each pair, the fluorescence image provides the answer as to whether an image actually contains any live cells or not (and/or how many live cells are present) while training is carried out using the corresponding brightfield image. Having performed such calibration, the resulting model can be used to determine, with a high success rate, whether a given sample contains live cells using only a brightfield image of dyed cells. Having identified the live cells, it is also possible to count the number of live cells within the image.

Figure 8:
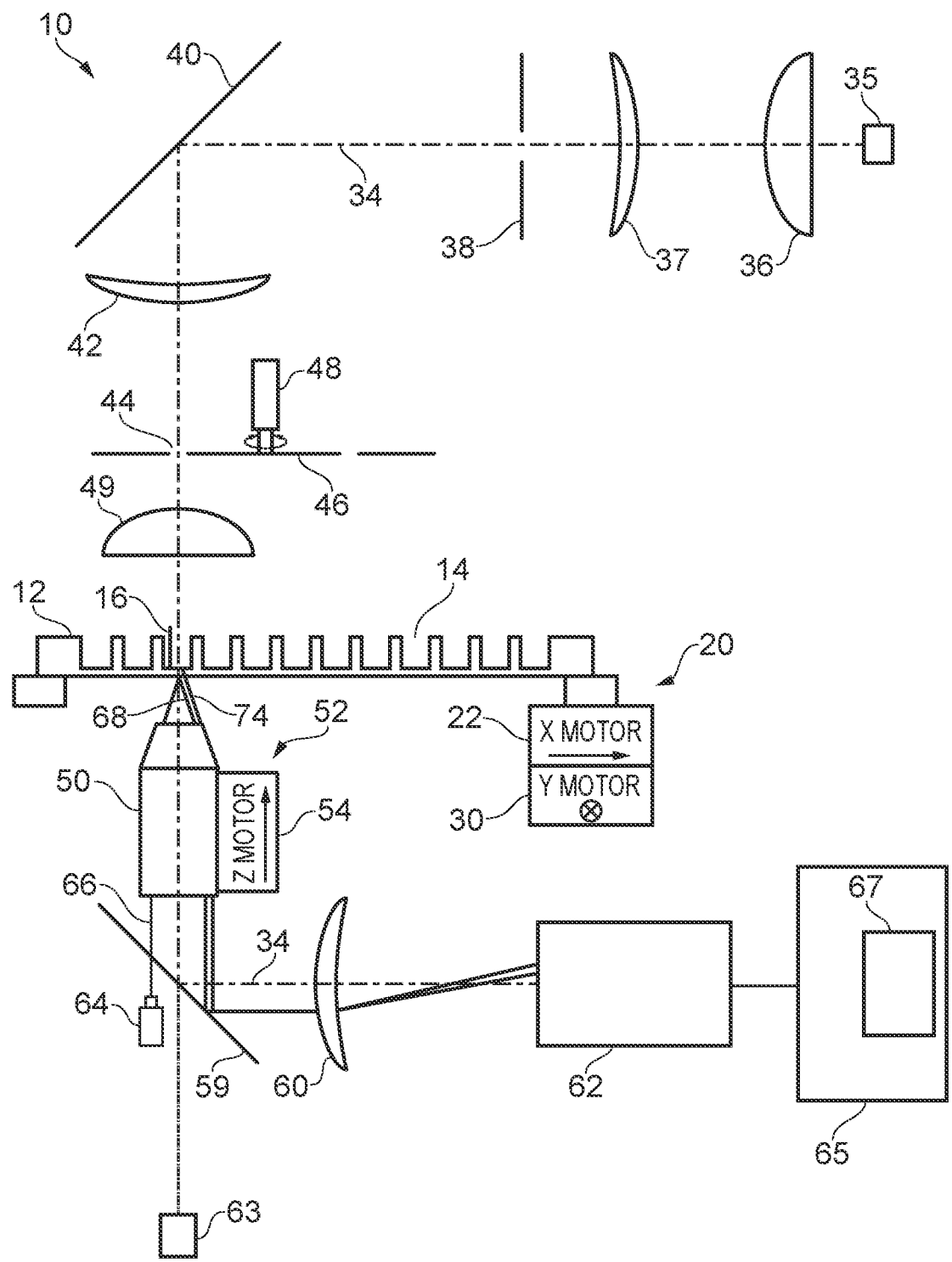
FIG. 8 illustrates an apparatus that is suitable for quickly generating pairs of fluorescence/brightfield image pairs for the training process.

FIG. 8 illustrates an apparatus that is suitable for quickly generating pairs of fluorescence/brightfield image pairs for the training process. A similar apparatus was originally described in more detail in granted patent GB2495537, the contents of which are incorporated herein by reference in their entirety.

As shown in FIG. 8, the apparatus 10 includes an XY stage 20 on which a microwell container 12 can be mounted. The XY stage 20 includes a X motor 22 and associated encoder 24 and feedback circuit 26 which can be controlled by a computer 28 to move the container 12 in the X direction, i.e. to the left and right as seen in FIG. 8. The XY stage 20 also includes a Y motor 30 and associated encoder 32 and feedback circuit 33 which can be controlled by the computer 28 to move the container 12 in the Y direction, i.e. in and out of the paper as seen in FIG. 8. The apparatus furthermore includes an optical system for illuminating a portion of the container and acquiring images of the illuminated portion.

Specifically, the optical system includes, in order along an optical axis 34 above the container 12: a light source 35 which may be implemented by an LED: a collecting lens 36; a collimating lens 37; an aperture 38 which may be adjustable; a mirror 40; a focusing lens 42; an aperture 44 which may be a fixed aperture or may be one of several apertures provided in a wheel 46 or strip movable by a motor 48 to select a particular aperture; and a condenser lens 49 which projects the light from the source 35 onto the biological sample in the microwell container 12.

The optical system furthermore includes, in order along an optical axis 34 below the container: an objective lens 50 which is mounted on a mechanical slide 52 including a motor 54 and associated encoder 56 and feedback circuit 58 which can be controlled by the computer 28 to move the objective lens 50 in the Z direction, i.e. up and down as seen in FIG. 8: a beam splitter 59 which may be implemented by a half-silvered mirror: a focusing lens 60; and a digital monochrome or colour camera 62.

Figure 9:
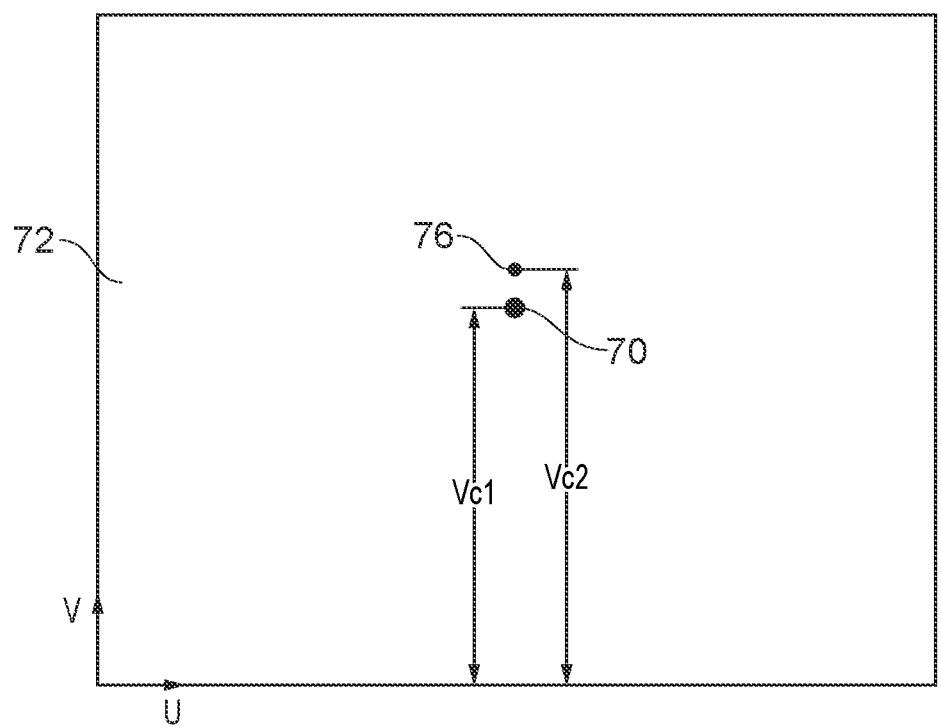
FIG. 9 shows the production of a spot on an image acquired by the camera.

In addition to being able to illuminate the sample and acquire images thereof, the optical system is also arranged to enable a determination to be made of the height of the portion of the floor 16 of the container 12 which is currently in the view of the camera 62 so that the focus of the image acquired by the camera 62 can be appropriately set. Specifically, a laser source 64 is disposed behind the beam splitter 59 and projects a laser beam 66 through the beam splitter 59 and the objective lens 50 so that it impinges at an inclined angle on the container 12 adjacent the optical axis 34. A first reflected beam 68 is produced at the underside of the container 12 and is reflected back through the objective lens 50 and passes into the camera 62 where, as shown in FIG. 9, it produces a first spot 70 in the image 72 acquired by the camera 62. Also, in the regions of the compartments 14 of the container 12, a second reflected beam 74 is produced at top side of the floor of the container 12 and is reflected back through the objective lens 50 and passes into the camera 62 where, as shown in FIG. 9, it produces a second spot 76 in the image 72 acquired by the camera 62.

For the purposes of fluorescence imaging, a fluorescence light source 63 can also be added to illuminate samples in the compartments 14 of the container 12 with light of a given wavelength. The biological sample may (depending on the characteristics of the imaging being performed) generate light of a difference wavelength. As will be known to the skilled person, when fluorescence imaging occurs, a filter could be employed (e.g. within the camera 62) to filter out light other than the light generated by the biological sample.

The captured images can be processed by processing circuitry 65 in order to generate a model using machine learning to determine whether a brightfield image contains live cells (and/or to count the number of live cells within a captures image). The generated model can be stored in storage circuitry 67.

This system can be used to quickly perform centralisation of images that are taken, as well as focusing of the images that are taken. In respect of centralisation, since the compartments 14 are curved, the distance between the objective lens 50 and the floor 16 of the compartment will increase and decrease as the XY stage 20 moves left and right. This causes the reflected spots 70, 76 in the image 72 to move (e.g. along the U axis in FIG. 9). By moving the XY stage 20 so that the spots 70, 76 are approximately in the centre of the image 72, the compartment 14 should be centralised within the image. Focusing on the contents of the compartments 14 can also be achieved quickly. A first initialisation step is performed by using brightfield imaging to take a series of images of a biological sample at different Z positions of the objective lens 50. A determination is then made (either automatically or from a user) as to which of the images (i.e. which Z position of the objective lens 50) produces the best focus on the contents of the compartment 14. Automated focusing for other compartments 14 (whose floors 16 are curved) can then take place. In particular, there is a linear relationship between the heights (e.g. Vc1, Vc2) along the V axis of the spots 70, 76 produced in the image 72 and the Z position of the objective lens 50. The relationship can be determined by considering the gradient of the change in V for a given spot as compared to the change in Z for the objective lens 50. It is then possible, for a given compartment 14 to adjust the Z position of the objective lens 50 to match the Z position that was determined as produced the best focus on the contents of the compartment 14 during the initialization step.

When the above apparatus is used to image cells that have been dyed using the functional dye Trypan blue, dead cells remain coloured by the dye and live cells expel the dye. Trypan blue is visible under brightfield imaging using the imaging apparatus 62 (which could either be a coloured imaging apparatus or a greyscale imaging apparatus). However, the dye has increased visibility under fluorescence imaging where dead cells are shown as solid masses. Live cells, which have been able to remove the Trypan blue, are either not shown in such images or are shown as 'halos'. It is therefore possible to identify live cells by looking for clusters of pixels. Having identified these regions of interest, it is possible to use machine learning to look for identifying features in the corresponding brightfield image that was taken approximately simultaneously. A training set of images might contain tens or possibly hundreds of pairs of fluorescence/brightfield images. A number of machine learning algorithms can be used. However, in some embodiments, a neural network such as a convolutional neural network (such as regions with convolutional neural networks, R-CNN) can be used to perform the training.

Figure 10:
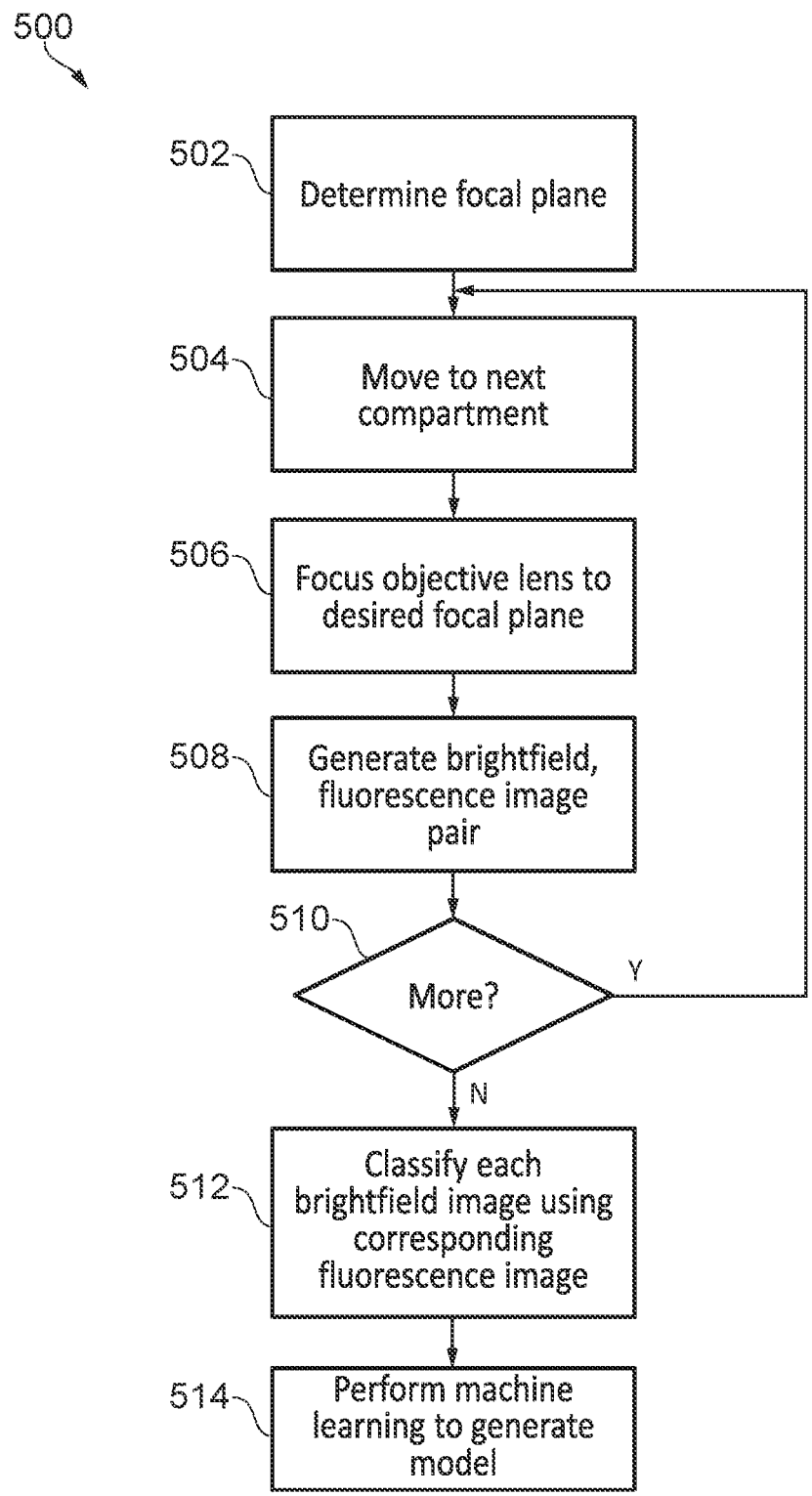
FIG. 10 illustrates a flow chart that shows a process of generating the training data to be provided to a machine learning algorithm in order to generate a model.

FIG. 10 illustrates a flow chart 500 that shows a process of generating the training data to be provided to a machine learning algorithm in order to generate a model. Prior to this process the microwell container 12 is provided in which the samples (e.g. cells) in the wells are stained with a functional dye such as an azo dye (e.g. Trypan blue). At a step 502, the focal plane is determined using the laser as previously described. This could take place using human intervention, for instance, by considering the first well of the microwell container 12. Having determined which of several images has the greatest focus, the Z position of the objective lens 50 is set. At a step 504, the XY stage 20 is moved so that the objective lens is centred on the next compartment 14 of the microwell container 12. At a step 506, the objective lens is adjusted so that it focusses on the focal plane identified in step 502, taking into account the curved floor 16 on which the sample rests. For instance, if the floor 16 is slightly raised as compared to the floor of the initial compartment (as determined from the laser) then the objective lens 50 is moved so that the chosen plane remains as the focal plane. At a step 508, a pair of images (one brightfield image, one fluorescence image) are produced at substantially the same time. At step 510, it is determined whether further compartments remain. If so, the process returns to step 504. Otherwise, at step 512, each brightfield image is classified using the fluorescence image (e.g. whether there are live cells, where the live cells are, how many live cells are present etc.). The information, together with the brightfield image is then provided to the machine learning algorithm in step 514 to perform machine learning and generate a model that, e.g. indicates whether a brightfield image contains live cells (or indicates the number of live cells, or indicates whether a given brightfield image is of a live cell).

Figure 11:
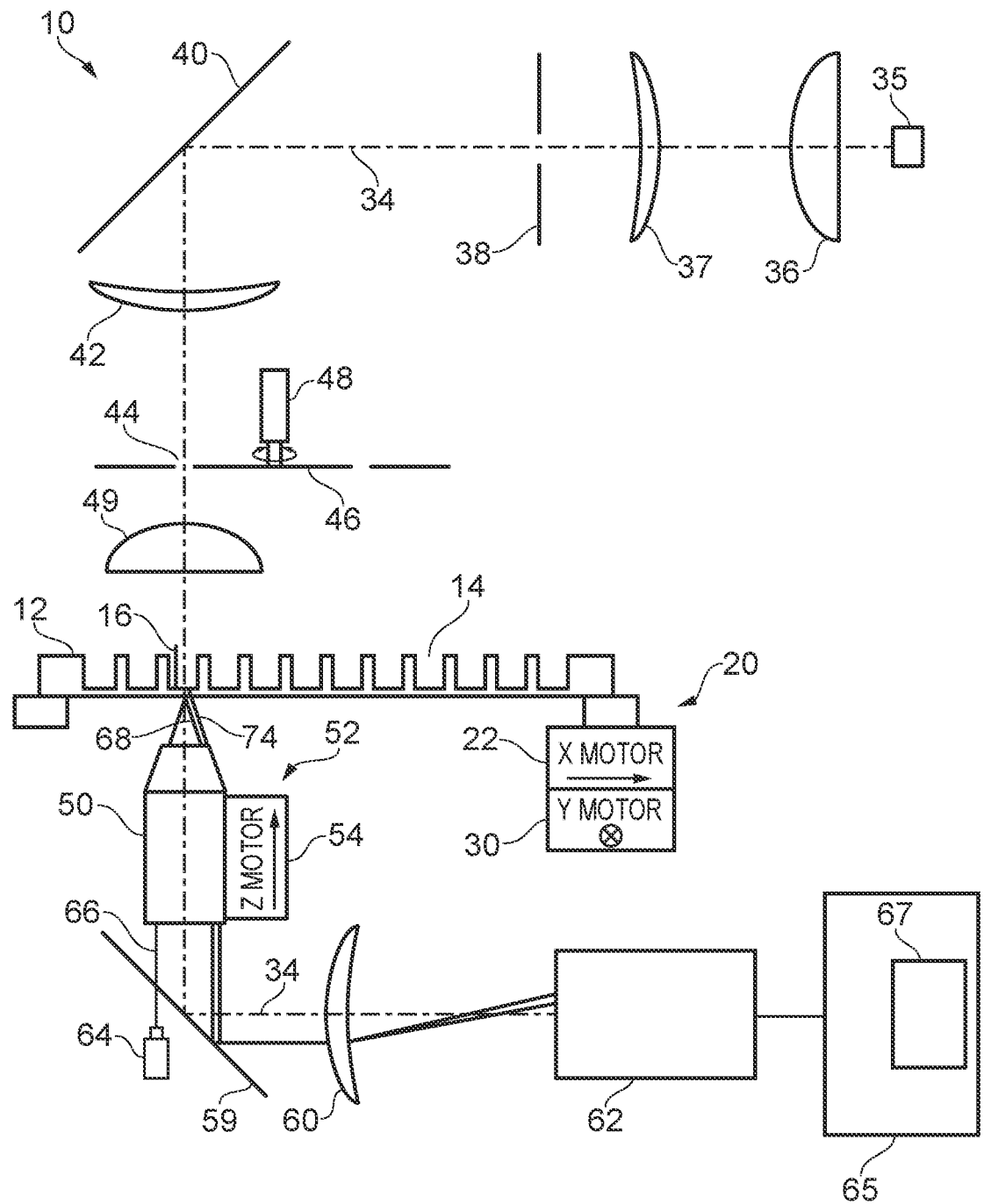
FIG. 11 shows a similar apparatus to that illustrated in FIG. 8 for making use of the model that has been devised.

FIG. 11 shows a similar apparatus to that illustrated in FIG. 8 for making use of the model that has been devised. In this example, the storage circuitry 67 stores the model that has been devised and the processing circuitry 65 uses the model on a captured brightfield image. For instance, if the model determines whether a given brightfield image contains a live cell then the model will provide this information when given a brightfield image of a cell that has been dyed with Trypan blue in the same manner in which the model was initially produced. Note that in this embodiment, no fluorescent light source is provided because fluorescence imaging is no longer required. Thus, the complexity and difficulty involved with fluorescence imaging can be avoided while still maintaining a high accuracy when performing image analysis on brightfield images.

Figure 12:
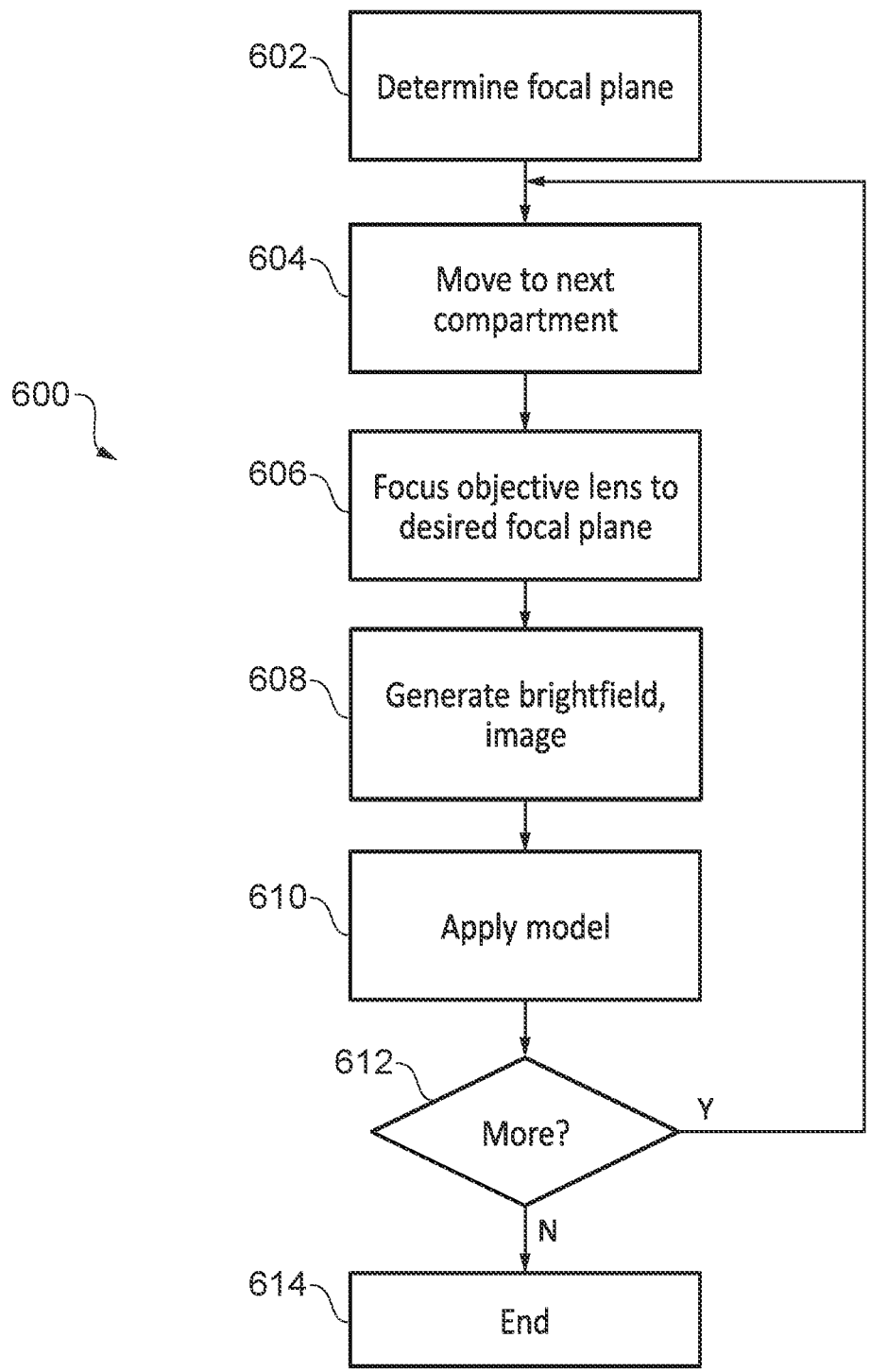
FIG. 12 illustrates a flow chart that shows a process of applying the generated model.

FIG. 12 illustrates a flow chart 600 that shows a process of applying the generated model. Prior to this process, a microwell container 12 is provided in which the samples (e.g. cells) in the microwell container 12 are stained with a functional dye such as an azo dye (e.g. Trypan blue). At a step 602, the focal plane is determined using the laser as previously described. This could take place using human intervention, for instance, by considering the first well of the microwell container 12. Having determined which of several images has the greatest focus, the Z position of the objective lens 50 is set. At a step 604, the XY stage 20 is moved so that the objective lens is centred on the next compartment 14 of the microwell container 12. At a step 606, the objective lens is adjusted so that it focusses on the focal plane identified in step 602, taking into account the curved floor 16 on which the sample rests. For instance, if the floor 16 is slightly raised as compared to the floor of the initial compartment (as determined from the laser) then the objective lens 50 is moved so that the chosen plane remains as the focal plane. At a step 608, a brightfield image is produced. At step 610, the model is applied to the brightfield image in order to produce a result. At step 612, it is determined whether further compartments 14 remain. If so, the process returns to step 604. Otherwise, the process ends at step 614.

Consequently, it can be seen how machine learning can be applied to forgo the complexities of brightfield imaging by using brightfield, fluorescence image pairs to train a model. The model can then be applied to brightfield images to gain at least some of the improved accuracy that can be achieved with fluorescence imaging, without the complex setup required for fluorescence imaging.

Although the above description has focused on the use of Trypan blue, it will be appreciated that the same process can be carried out using other azo dyes or indeed other functional dyes that can be used to indicate a particular characteristic of a cell. Clearly, when the above technique is used to identify whether a given cell is alive or not, the same process can be repeated for multiple cells in a brightfield image in order to determine how many live cells exist.

In the present application, the words "configured to . . . " are used to mean that an element of an apparatus has a configuration able to carry out the defined operation. In this context, a "configuration" means an arrangement or manner of interconnection of hardware or software. For example, the apparatus may have dedicated hardware which provides the defined operation, or a processor or other processing device may be programmed to perform the function. "Configured to" does not imply that the apparatus element needs to be changed in any way in order to provide the defined operation.

Although illustrative embodiments of the invention have been described in detail herein with reference to the accompanying drawings, it is to be understood that the invention is not limited to those precise embodiments, and that various changes, additions and modifications can be effected therein by one skilled in the art without departing from the scope and spirit of the invention as defined by the appended claims. For example, various combinations of the features of the dependent claims could be made with the features of the independent claims without departing from the scope of the present invention.

What is claimed is:

1. A calibration apparatus comprising:
   estimation circuitry comprising an optical microscope and an image capturing device configured to capture a brightfield image of a dyed biological sample using the optical microscope, the estimation circuitry configured to estimate, based on a calibration factor, an estimated number of cells of a first type in the dyed biological sample containing an unknown number of cells by counting the cells in the brightfield image;
   determination circuitry comprising a fluorescence microscope and an image capturing device configured to capture a fluorescence image of the dyed biological sample using the fluorescence microscope, the determination circuitry configured to determine an actual number of cells of the first type in the dyed biological sample by counting the cells present in the fluorescence image; and processing circuitry configured to adjust the calibration factor until the estimation circuitry and the determination circuitry both produce results for the estimated number of cells of the first type that approach one another, wherein the processing circuitry comprises a machine learning model trained using pairs of brightfield images and fluorescence images that have estimated numbers of cells that approach each other, and wherein the processing circuitry is further configured to use the calibration factor to estimate, from brightfield images of additional dyed biological samples without use of the fluorescence microscope, estimated numbers of cells of the first type in the additional dyed biological samples.

2. The calibration apparatus of claim 1, further comprising:

further determination circuitry configured to determine a total number of cells in the dyed biological sample, and wherein the estimation circuitry is further configured to estimate, based on the calibration factor, a second estimated number of cells of a second type in the dyed biological sample containing the unknown number of cells.

3. The calibration apparatus of claim 2, wherein the estimation circuitry is further configured with the processing circuitry to determine the estimated number of cells of the first type and the estimated number of cells of the second type in the dyed biological sample one or more times, based on a different value of the calibration factor for each of the one or more times, until a sum of: (i) the estimated number of the cells of the first type and (ii) the estimated number of the cells of the second type approaches the total number of the cells in the biological sample.

4. The calibration apparatus of claim 3, wherein the estimation circuitry is configured to:

determine the estimated number of the cells of the second type by counting colourless cells in the brightfield image of the dyed biological sample; and determine the estimated number of the cells of the first type by counting contrasted cells in the brightfield image of the dyed biological sample.

5. The calibration apparatus of claim 3, wherein the brightfield image of the dyed biological sample is a colour image.

6. The calibration apparatus of claim 3, wherein the brightfield image of the dyed biological sample is a greyscale image.

7. The calibration apparatus of claim 1, wherein the determination circuitry is configured to determine the actual number of the cells of the first type in the dyed biological sample based on a fluorescent intensity.

8. The calibration apparatus of claim 1, wherein the estimation circuitry and the determination circuitry operate in parallel.

9. The calibration apparatus of claim 2, wherein the second type of cells is living cells.

10. The calibration apparatus of claim 1, wherein the first type of cells is dead cells.

11. A calibration method comprising:

performing, using an optical microscope and a brightfield imaging process, an estimation process on a dyed biological sample containing an unknown number of cells to estimate, based on a calibration factor, an estimated number of cells of a first type in the dyed biological sample;

performing, using a fluorescence microscope and a fluorescence imaging process, a determination process on the dyed biological sample to determine an actual number of the cells of the first type in the dyed biological sample;

repeating at least a portion of the estimation process one or more times, based on a different value of the calibration factor for each of the one or more times, until the estimated number of the cells of the first type approaches the actual number of cells of the first type, wherein an adjusted calibration factor is generated; and using the optical microscope and the adjusted calibration factor to estimate, from brightfield images of additional dyed biological samples, estimated numbers of cells of the first type in the additional dyed biological samples.

12. The calibration method of claim 11, wherein use of the fluorescence microscope is avoided when estimating the estimated number of cells of the first type in the additional dyed biological samples.

* * * * *